US006727089B2

(12) United States Patent
Ho et al.

(10) Patent No.: US 6,727,089 B2
(45) Date of Patent: Apr. 27, 2004

(54) CULTURING CHAMBER ON MICROSCOPE STAGE

(75) Inventors: Chung-Liang Ho, Taipei (TW); Tun-Yi Mou, Tainan (TW)

(73) Assignee: National Cheng Kung University, Tainan (TW)

( * ) Notice: Subject to any disclaimer, the term of this patent is extended or adjusted under 35 U.S.C. 154(b) by 0 days.

(21) Appl. No.: 10/320,552

(22) Filed: Dec. 17, 2002

(65) Prior Publication Data

US 2003/0113905 A1 Jun. 19, 2003

(30) Foreign Application Priority Data

Dec. 19, 2001 (TW) ........................................ 90222311 U

(51) Int. Cl.$^7$ .............................................. C12M 1/34
(52) U.S. Cl. ................... 435/288.3; 435/288.7; 435/305.1; 435/305.4; 356/244; 359/398
(58) Field of Search ............................ 435/288.3, 288.7, 435/305.1, 305.4; 356/244, 246; 359/398

(56) References Cited

U.S. PATENT DOCUMENTS

| 3,726,597 | A | * | 4/1973 | Dvorak et al. ............... 356/244 |
| 4,734,372 | A | * | 3/1988 | Rotman ........................ 435/29 |
| 4,974,952 | A | * | 12/1990 | Focht .......................... 359/398 |
| 5,665,599 | A | * | 9/1997 | Minuth ..................... 435/288.3 |
| 5,759,846 | A | * | 6/1998 | Stoppini et al. .......... 435/284.1 |
| 5,851,489 | A | * | 12/1998 | Wolf et al. ............... 422/82.02 |
| 6,448,063 | B2 | * | 9/2002 | Tominaga et al. ........ 435/284.1 |
| 6,586,235 | B1 | * | 7/2003 | Banes ...................... 435/293.1 |

* cited by examiner

*Primary Examiner*—David A. Redding
(74) *Attorney, Agent, or Firm*—Fei-Fei Chao; Venable LLP

(57) ABSTRACT

A culturing chamber is a closed system to culture cells on a microscope stage for a long time and consists of base (10), a compartment layer (20), and a lid (30) sealingly and detachably combined together. The lid (30) is able to be selectively opened or closed to make the operation such as cell injection convenient. An electronic signal device containing a mult-operational system is applied to the culture chamber to maintain the living circumstance steady for the cells, so that the cultured cells can live long on the microscope stage and be observed and cultured at the same time.

11 Claims, 5 Drawing Sheets

000# CULTURING CHAMBER ON MICROSCOPE STAGE

BACKGROUND OF THE INVENTION

1. Field of the Invention

The present invention relates to a culturing chamber applied on a microscope stage, and more particularly to a culturing chamber, which can support the growth of cells on a microscope stage for a long time.

2. Description of Related Art

A culturing device is commonly used to study activities of microscopic organisms, cancer cells, embryo tissue etc, and is an important item of equipment for biotechnology.

There are two kinds of conventional culturing devices presently in use:

1. Culturing box: the culturing box is an old established way to culture cells, but its drawback is that the cells cannot be studied on the microscope stage at the same time. Therefore, the cells have to be removed from the culture box to the microscope stage, whereafter they easily deteriorate because temperature, humidity, and condensation of carbon dioxide of room are changed when the cells are placed on the microscope stage. Cells can not be observed on the microscope stage for a long time.

2. Culturing chamber: the culturing chamber enables the cells to be observed and cultured on the microscope stage at the same time but it can not keep the cells alive for a long time. Additionally, consumption of the carbon dioxide is huge when keeping the cells alive so that operational cost for culturing the cells is high. Moreover, structure of the culturing chamber is designed in either an open-type for changing the content of the culturing chamber or a closed-type, which can not be opened. Therefore, the conventional culturing chamber can not be selectively operated between the open-type and the closed-type and has limitations when being used.

The present invention has arisen to mitigate and/or obviate the disadvantages of the conventional culturing chamber.

SUMMARY OF THE INVENTION.

The main objective of the present invention is to provide a culturing chamber, which extends cell life for a long time and reduces operational cost for culturing cells.

Further benefits and advantages of the present invention will become apparent after a careful reading of the detailed description with appropriate reference to the accompanying drawings.

DETAILED DESCRIPTION OF THE INVENTION

Figure 1:
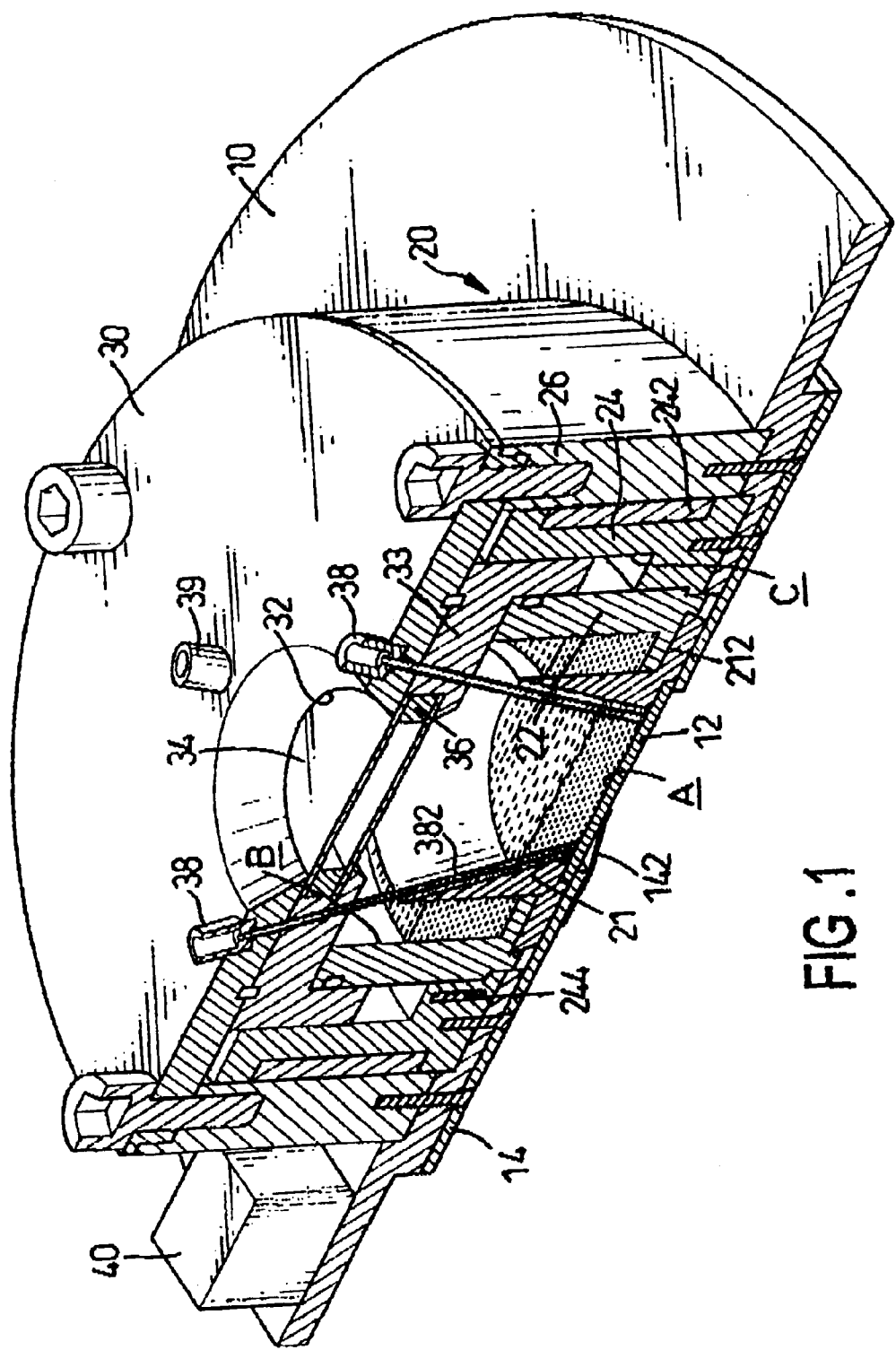
FIG. 1 is a perspective view in partial cross-section of a culturing chamber in accordance with the present invention.
Figure 2:
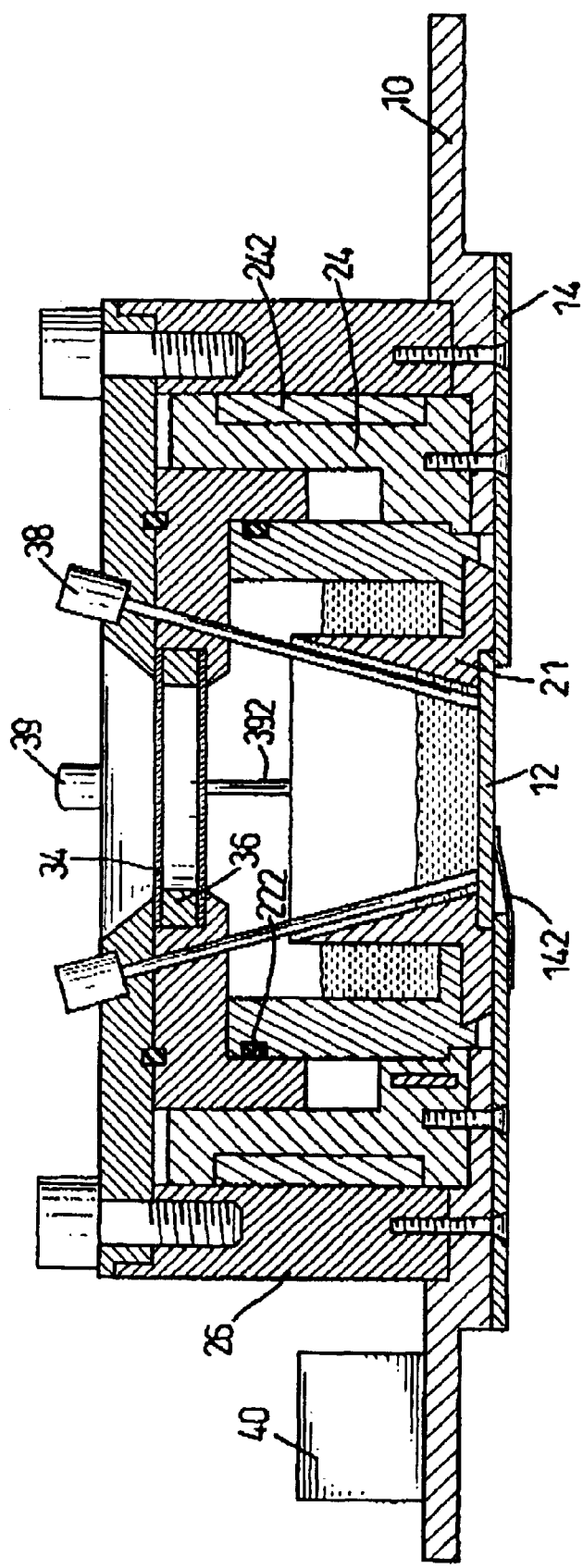
FIG. 2 is a cross-sectional side plan view of the culturing chamber in FIG. 1.

With reference to FIGS. 1 and 2, a culturing chamber in accordance with the present invention comprises a base (10), a compartment layer (20) and a lid (30).

The base (10) is a circular board having a top face and a bottom face and has a hole (not numbered) defined in the center of the base (10). An annular circuit board (14) is attached on the bottom face of the base (10) by screws and has a central hole (not numbered) defined in the circuit board (14), wherein the central hole has a diameter smaller than a diameter of the hole of the base (10) and is concentric with the hole of the base (10). Therefore, the circuit board (14) partially covers the bole of the base (10). A bottom plate (12) is electrothermally conductive and is mounted on circuit board (14) to cover the central hole in the circuit board (14). A conductive sheet (142) extends between the circuit board (14) and the bottom plate (12).

The compartment layer (20) is hermetically sandwiched between the base (10) and the lid (30) and has an inner wall (21), a sealing wall (22), a heating wall (24), and a thermal preservative wall (26). The inner wall (21) erects on the circuit board (14) around the bottom plate (12) to construct an inner tank (A) for storing culturing fluid and further has a pedestal (212) extending from the foot of the inner wall (21). The sealing wall (22) concentrically erects around the inner wall (21) on the circuit board (14) and keeps a distance from the inner wall (21) to construct a water sink (B), wherein the water sink (B) provides a thermal preservative efficiency to the culturing chamber. Additionally the sealing wall (22) further has a protruding area (not numbered) overlapping and contacting with the pedestal (212) of the inner wall (21). A gasket (222) is partially embedded in an outer periphery of the sealing wall (22). The heating wall (24) also concentrically erects around the sealing wall (22) with a distance from the sealing wall (22) and has an enlarged bottom portion (not numbered) extending to contact with the sealing wall (22) to construct a gap (C) between the sealing wall (22) and the heating wall (24). A heating resistor (242) is embedded in the heating wall (24) near an outside periphery of the heating wall (24) and electrically connects with the circuit board (14). A thermal sensor (244) is embedded in the heating wall (24) at the enlarged bottom portion and communicates with the circuit board (14) to transmit the temperature signal. The thermal preservative wall (26) erects adjacent to the heating wall (24) to keep the culturing chamber steady warm. Moreover, the inner wall (21) has a height lower than the sealing wall (22) so that the inner tank (A) communicates with the water sink (B).

The lid (30) corresponding to the compartment layer (20) is a circular plate and mounted on the compartment layer (20) by screws. The lid (30) has an opening (32) defined in the center of the lid (30) to align with the inner tank (A). A L-shaped wedge (33) is attached under the lid (30) and has a first end inserting into the gap (C) of the compartment layer (20) and a second end extending to the opening (32). A window (34) engages with the second end of the wedge (33) to cover the opening (32). The window (34) is composed of two layers of transparent and thermal-conductive glass spaced apart from each other to prevent thermal loss of the culturing chamber and an annular heating resistor (36) sandwiched between the two layers of glass to provide heat and avoid misting on the glass. At least one aperture (38) for liquid is defined in the lid (30) to communicate with the inner tank (A) and each aperture (38) has a liquid guiding tube (382) inserting into the culturing liquid. In the embodiment shown in the drawings, two apertures (38) are defined in opposite sides around the opening (32). At least one gas aperture (39) is defined in the lid (30) to communicate with an inner space of the culturing chamber for gas to flow therethrough. In the embodiment shown in the drawings, two gas apertures (39) are oppositely defined in the lid (30)

around the opening (32). Each gas aperture (39) is 90° biased to a respective adjacent inlet (38) and has a gas guiding tube (392) inserting into the culturing liquid. Moreover, the lid (30) further has a circuit board attached to the circular plate. The heating resistor (36) and a thermal sensor (not shown) are both attached on the lid (30) and electrically connected to the circuit board.

Figure 3:
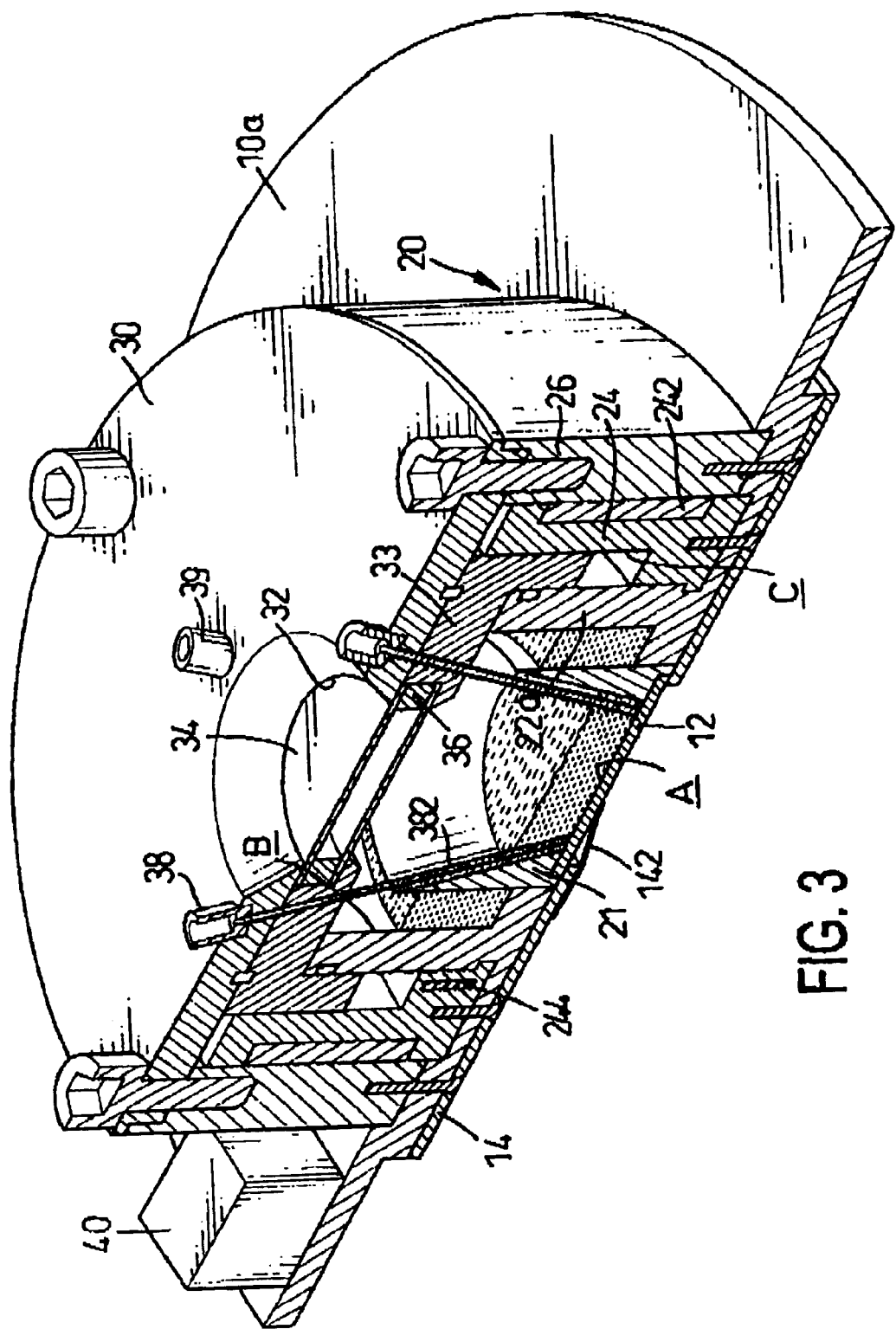
FIG. 3 is a cross-sectional side plan view of another embodiment of the culturing chamber in accordance with the present invention.

With reference to FIG. 3, another embodiment of the culturing chamber in the present invention shows that the sealing wall (22a) is formed as a single piece on the base (10a). Other elements of the culturing chamber can be detachably or immovably constructed on the base (10a).

When the culturing chamber is operated, an electronic signal device (40) is connected with the culturing chamber to automatically control the temperature, humidity, gas change and liquid change and to keep the cell growth in a desired circumstance.

Figure 4:
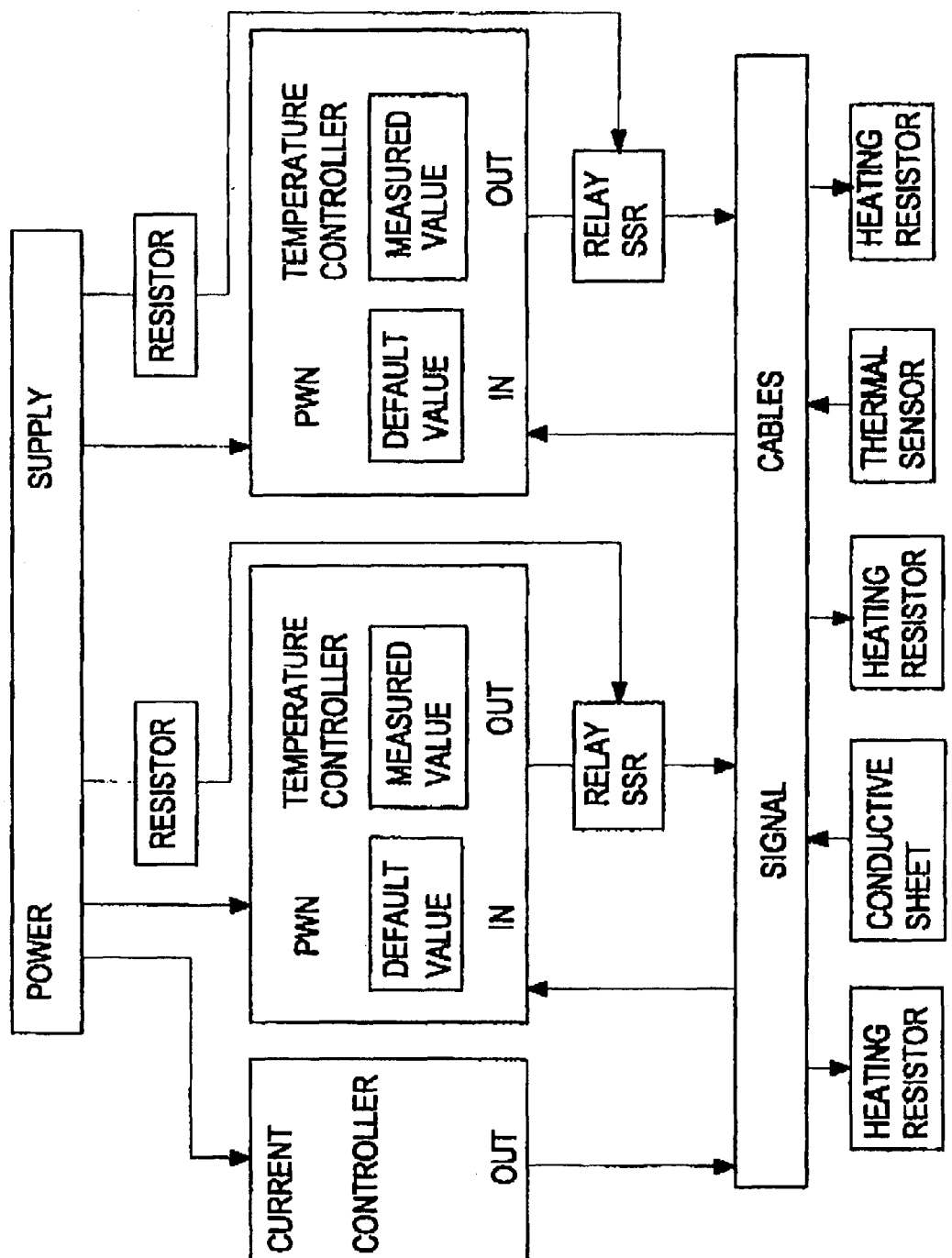
FIG. 4 is a block diagram of a circuit applied to the culturing chamber in the present invention.

With reference to FIG. 4 in coordination with FIG. 1, a power supply is connected to a current controller and two temperature controllers respectively to provide power to operate the culturing system and activate the heating resistors to control the temperature. Each temperature controller has an inlet and an outlet, wherein each outlet is connected with a relay to activate the heating resistors via multiple signal cables. The conductive sheet (142) and the thermal sensor (244) are connected to the signal cables respectively to transmit the temperature signals back to the temperature controllers via the inlets. Each temperature controller compares the temperature signal with a default value and sends a feedback signal to the relay to control the heating resistor. A current resistor is settled between the current supply and the relay to reduce the deviation of the temperature change.

The temperature controller is a pulse-width modulation (PWM) and the relay controlled by the temperature controller is a static shift register (SSR) to set an optimal approaching curve to make the temperature deviation less than 0.1° C. within 10 minutes.

Figure 5:
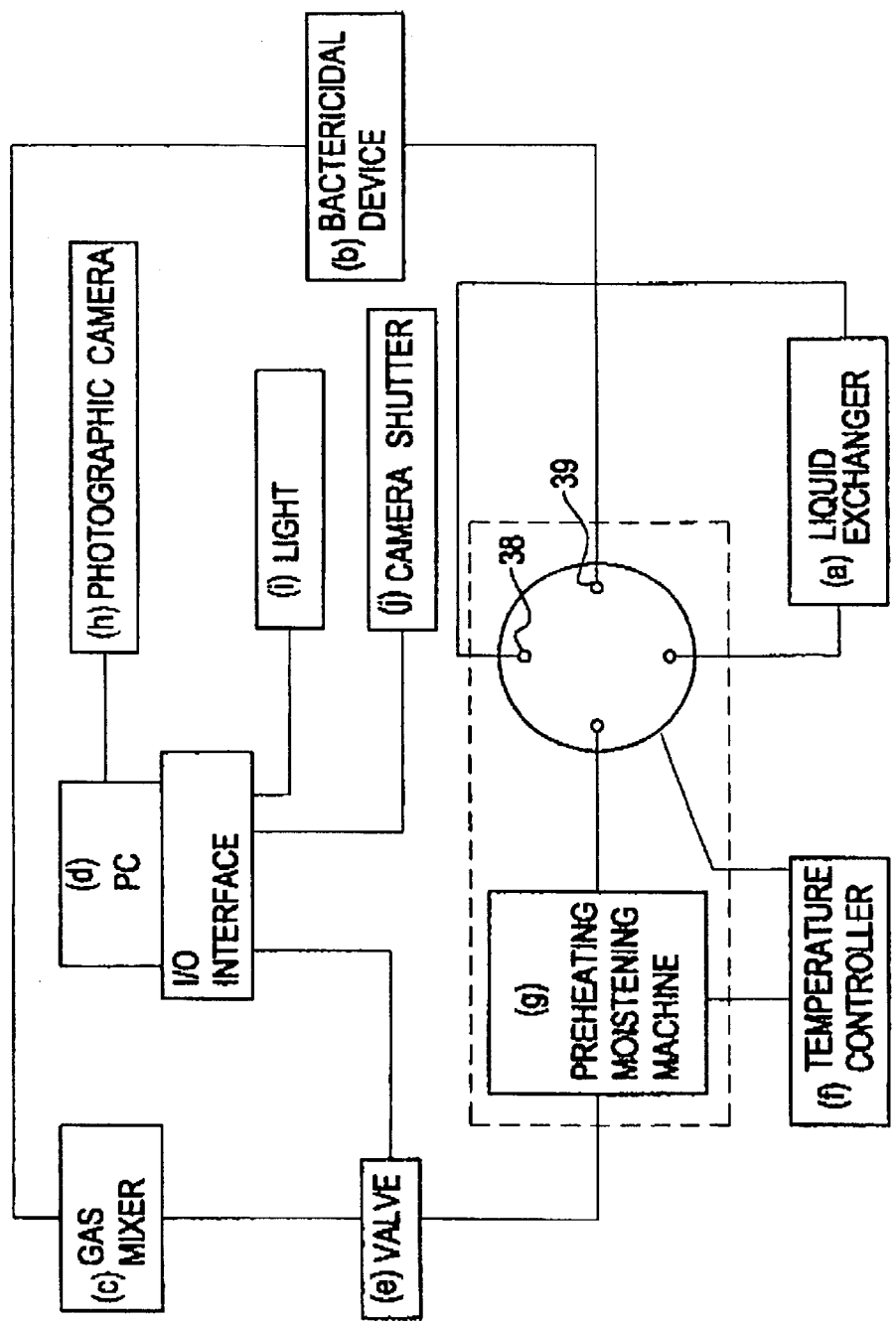
FIG. 5 is a schematic view of the culturing chamber to show connections between equipment applied to the culturing chamber.

With reference to FIG. 5 in coordination with FIG. 1, the two apertures (38) are connected with an automatic liquid exchanger (a) to construct a loop to change the culturing liquid in the inner tank (A) after a period of time. One of the gas apertures (39) is connected with a bactericidal device (b) to disinfect air drawn from the culturing chamber and then guided to a gas mixer (c) to mix the air with carbon dioxide. When the air is well mixed with the carbon dioxide, a personal computer (d) adjusts a valve (e) to control flow of a desired quantity of the mixed air into the culturing chamber.

Additionally, the thermal sensor (244) detects the temperature of the culturing chamber and transmits the temperature signal to the temperature controller (f). Then, the temperature controller (f) activates a preheating moistening machine (g) to adjust the mixed air to a desired temperature and a desired humidity to reduce deviation impact before sending to the culturing chamber.

The personal computer (d) further connects with a photographic camera (h) with a light (i) and a camera shutter (j) mounted on the culturing chamber to take pictures of the changes of the cultured cells.

According to the above description, there are three independent temperature controlling units in the embodiment of the present invention;

1. Preheating the mixed gas: the mixed gas of air and carbon dioxide is preheated and moistened by the preheating moistening machine (g) before the mixed gas is guided into the culturing chamber to avoid the temperature and humidity changes.

2. Water sink: the water sink (B) is filled with preheated water to increase the heat capacity in the culturing chamber and reduce the temperature deviation. Additionally, the water sink (B) provides enough humidity to the space of the culturing chamber to make the air saturated and keeps the culturing liquid in the inner tank (A) from having no vaporization.

3. Air-tight culturing chamber; the culturing chamber is airtight to avoid heat loss and the thermal preservative wall (26) reduces the temperature deviation, therefore, the temperature is steady in the culturing chamber.

The culturing chamber in the present invention has the following advantages:

1. The lid (30) is able to be selectively opened to operate treatment such as an injection to the cells or to be closed to make the culturing chamber airtight. The lid (30) is made of Teflon™ and the window (34) mounted on the lid (30) is made of two layers of thermal-conductive glass and heated to keep the culturing chamber warn and avoid misting.

2. The temperature controller of pulse-width modulation (PWM) and the relay of static shift register (SSR) control the temperature deviation to less than 0.1° C. within 10 minutes. Moreover, three independent temperature controlling units are incorporated with the temperature controller to ensure the cultured cells live in a stable circumstance for a long period.

3. When the lid (30) is mounted on the compartment layer (20) to make the culturing chamber closed and airtight. The carbon dioxide is recycled in the loop of the gas apertures (39), the bactericidal device (b), and the gas mixer (c). Therefore, consumption of the carbon dioxide is decreased to reduce the operational cost for culturing.

In order to prove the efficiency of the culturing chamber, an appendix of "the effect of acrylamide on slow axonal transport: a real-time, live-cell model to study slow axonal transport" is attached.

Although the invention has been explained in relation to its preferred embodiment, it is to be understood that many other possible modifications and variations can be made without departing from the spirit and scope of the invention as hereinafter claimed.

What is claimed is:

1. A culturing chamber comprising:
   a base (10) with a top face and a bottom face having:
      a hole defined in the base (10);
      a circuit board (14) having a central hole and partially covering the hole of the base (10) by attaching to the bottom face of the base (10);
      a conductive bottom plate (12) mounted on the top face of the base (10) to cover the central hole in the circuit board (14); and
      a conductive sheet (142) extends between the circuit board (14) and the bottom plate (12);
   a compartment layer (20) hermetically mounted on the base (10) and having
      an inner wall (21) erected on the base (10) around the bottom plate (12) to construct an inner tank (A);
      a sealing wall (22) erected around the inner wall (21) on the base (10) and keeps a distance to the inner wall (21) to construct a water sink (B), wherein the water sink (B) communicates with the inner tank (A) and adapted to store water to provide a thermal preservative efficiency to the culturing chamber;
      a heating wall (24) erected around the sealing wall (22) and having a heating resistor (242) and a thermal sensor (244) both embedded in the heating wall (24) and both communicated with the circuit board (14); and a thermal preservative wall (26) erecting adjacent to the heating wall (24) to keep the culturing chamber constantly warm;

a lid (30) mounted on the compartment layer (20) and having an opening (32) defined in the lid (30) to align with the inner tank (A); and a window (34) mounted on the lid (30) to cover the opening (32) and composed of at least one conductive glass, the lid (30) having at least two apertures (38) and at least two gas apertures (39) defined in the lid (30) to communicate with the inner tank (A), wherein each aperture (38) and gas aperture (39) has a guiding tube (382, 392) inserting into the culturing liquid; and an electronic signal device (40) connected with base (10), the compartment layer (20) and the lid (30) of the culturing chamber to automatically control the temperature, humidity, gas change and liquid change in the culturing chamber and to keep the cell growth in a desired circumstance.

2. The culturing chamber as claimed in claim 1, in which a gap (C) is constructed between the sealing wall (22) and the heating wall (24); and a L-shaped wedge (33) is attached under the lid (30) and has a first end inserting into the gap (C) of the compartment layer (20) and a second end extending to the opening (32), wherein the window (34) engages with the second end of the wedge to cover the opening (32).

3. The culturing chamber as claimed in claim 2, in which a gasket (222) is attached on the sealing wall (22) to contact with the first end of wedge (33).

4. The culturing chamber as claimed in claim 1, wherein the base (10) and the bottom plate (12) are detachably engaged.

5. The culturing chamber as claimed in claim 1, wherein the inner wall (21) and the bottom plate (12) are detachably engaged.

6. The culturing chamber as claimed in claim 1, wherein a window (34) is detachably mounted on the lid (30).

7. The culturing chamber as claimed in claim 1, wherein the lid (30) is a circular plate and further has a circuit board attached to the circular plate;

a heating resistor (36) attached to the circular plate and electrically connected to the circuit board; and a thermal sensor attached to the circular plate and electrically connected to the circuit board.

8. The culturing chamber as claimed in claim 1, wherein the electronic signal device (40) comprises:

a power supply connected to a current controller and two temperature controllers respectively, wherein each temperature controller has an inlet and an outlet;

a relay connected with the outlet of each respective temperature controller to activate the heating resistors via multiple signal cables;

the conductive sheet (142) and the thermal sensor (244) connected to the signal cables respectively to transmit temperature signals back to the temperature controller via the inlets of the temperature controllers, wherein each temperature controller compares the temperature signal with a default value and sends a feedback signal to the relay to control the heating resistor.

9. The culturing chamber as claimed in claim 1, wherein the two apertures (38) connected with an automatic liquid exchanger (a); and one of the gas apertures (39) is connected with a bactericidal device (b) to disinfect air drawn from the culturing chamber and then guided to a gas mixer (c) to mix the air with carbon dioxide, then the air well-mixed with the carbon dioxide is guided into the culturing chamber via the other of the gas aperture (39); and a valve (e) is attached between the gas mixer (c) and the culturing chamber to adjust the quantity of the mixed gas of the air and the carbon dioxide.

10. The culturing chamber as claimed in claim 9, wherein the electronic signal device further comprises a preheating moistening machine (g) connected with the one of the gas apertures (39) served as an inlet to adjust the air to a desired temperature and a desired humidity to reduce deviation impact on the air before sending the air to the culturing chamber.

11. The culturing chamber as claimed in claim 10, wherein the electronic signal device further comprises:

a personal computer (d) connected with a photographic camera (h) with a light (i) and a camera shutter (j) mounted on the culturing chamber to take pictures of the changes of the cultured cells, wherein the personal computer (d) further connects to and controls the valve (e).

* * * * *